(12) United States Patent
Ax et al.

(10) Patent No.: US 8,984,069 B2
(45) Date of Patent: Mar. 17, 2015

(54) TASKFLOW UNIT FOR CONTROLLING COMPUTER-AIDED MEDICAL TASKS WITHIN A MEDICAL COMPUTER NETWORK

(75) Inventors: Antonius Ax, Effeltrich (DE); Karlheinz Dorn, Kalchreuth (DE); Vladyslav Ukis, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 361 days.

(21) Appl. No.: 12/836,662

(22) Filed: Jul. 15, 2010

(65) Prior Publication Data
US 2011/0029623 A1 Feb. 3, 2011

(30) Foreign Application Priority Data
Jul. 29, 2009 (DE) .......................... 10 2009 035 098

(51) Int. Cl.
G06F 15/16 (2006.01)
G06F 15/173 (2006.01)
G06F 9/48 (2006.01)
G06F 19/00 (2011.01)

(52) U.S. Cl.
CPC ............ G06F 9/4843 (2013.01); G06F 19/325 (2013.01)
USPC .......................................... 709/206; 709/223

(58) Field of Classification Search
None
See application file for complete search history.

(56) References Cited

U.S. PATENT DOCUMENTS

| | | | |
|---|---|---|---|
| 2001/0031997 A1* | 10/2001 | Lee .................................. | 607/59 |
| 2001/0051881 A1* | 12/2001 | Filler ............................... | 705/3 |
| 2002/0103675 A1* | 8/2002 | Vanelli ............................ | 705/3 |
| 2004/0103413 A1 | 5/2004 | Mandava | |
| 2004/0122705 A1* | 6/2004 | Sabol et al. ...................... | 705/2 |
| 2005/0080330 A1* | 4/2005 | Masuzawa et al. ........... | 600/407 |
| 2005/0182846 A1* | 8/2005 | Schofield et al. ............ | 709/232 |
| 2005/0209889 A1* | 9/2005 | Funahashi ........................ | 705/3 |
| 2006/0095429 A1* | 5/2006 | Abhyankar et al. ............ | 707/7 |
| 2006/0261145 A1* | 11/2006 | Robertson et al. ............ | 235/375 |
| 2006/0282302 A1* | 12/2006 | Hussain ............................ | 705/9 |
| 2007/0027711 A1* | 2/2007 | Beraja et al. .................... | 705/2 |
| 2007/0214235 A1* | 9/2007 | Woods et al. ................. | 709/217 |
| 2007/0283320 A1* | 12/2007 | Dorn et al. .................... | 717/107 |
| 2008/0010089 A1* | 1/2008 | DiMaggio et al. ............... | 705/2 |
| 2008/0103833 A1* | 5/2008 | Miglietta et al. .................. | 705/3 |
| 2008/0132781 A1* | 6/2008 | Redel ............................ | 600/419 |
| 2008/0141213 A1* | 6/2008 | Dorn et al. .................... | 717/100 |
| 2008/0141234 A1* | 6/2008 | Becker et al. ................. | 717/162 |
| 2008/0141250 A1* | 6/2008 | Dorn et al. .................... | 718/100 |
| 2008/0208750 A1* | 8/2008 | Chen .............................. | 705/50 |
| 2009/0024413 A1* | 1/2009 | Haider et al. ..................... | 705/3 |
| 2009/0157695 A1* | 6/2009 | Roberts .......................... | 707/10 |

FOREIGN PATENT DOCUMENTS

| | | |
|---|---|---|
| DE | 102009010889 A1 * | 9/2010 |
| EP | 1583017 A2 * | 10/2005 |
| EP | 1850289 A1 * | 10/2007 |
| WO | WO 2009135124 A3 * | 1/2010 |

* cited by examiner

Primary Examiner — Kostas Katsikis
(74) Attorney, Agent, or Firm — Harness, Dickey & Pierce, P.L.C.

(57) ABSTRACT

A taskflow unit that assigns tasks to different software units in a medical computer network. The taskflow unit merges tasks to form at least one taskflow within the medical computer network. The taskflow unit is installed on an application server within the computer network.

17 Claims, 1 Drawing Sheet

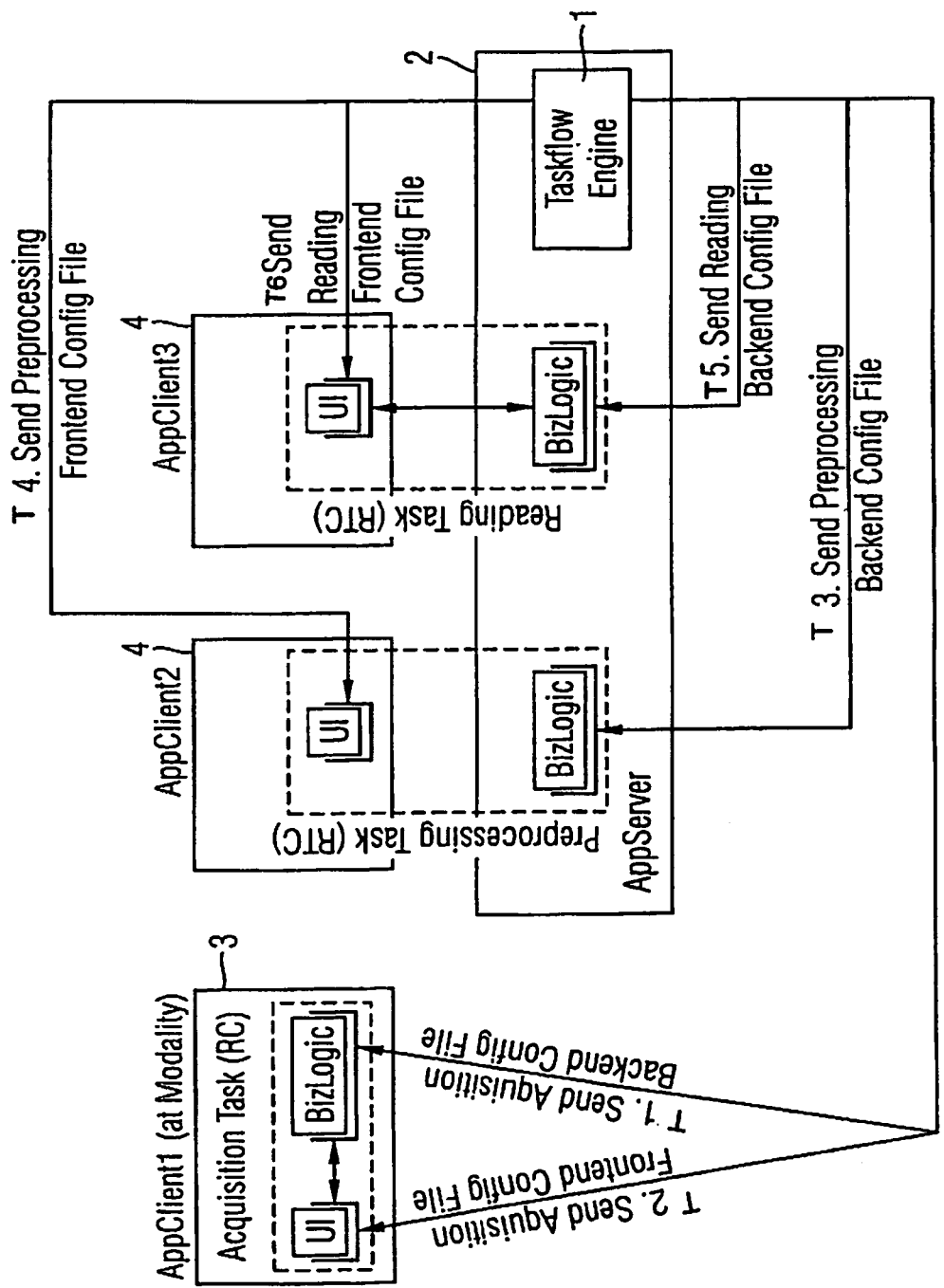

TASKFLOW UNIT FOR CONTROLLING COMPUTER-AIDED MEDICAL TASKS WITHIN A MEDICAL COMPUTER NETWORK

PRIORITY STATEMENT

The present application hereby claims priority under 35 U.S.C. §119 on German patent application number DE 10 2009 035 098.5 filed Jul. 29, 2009, the entire contents of which are hereby incorporated herein by reference.

FIELD

At least one embodiment of the invention generally relates to a unit having at least one device and/or module for controlling computer-aided medical tasks within a medical computer network as well as to a corresponding method.

At least one embodiment of the invention generally relates to a method and unit for fault-tolerant, workplace-independent, end-to-end processing of tasks in a medical taskflow, which tasks have different layer distribution architectures.

BACKGROUND

A workflow or, as the case may be, taskflow describes working sequences or, as the case may be, the processing sequence for different tasks. In the in the information technology (IT) field a template (model or predefined standard format) defines specific workflows or, as the case may be, taskflows which can be reused or repeated for different applications.

Medical tasks generally consist of three software units or layers: presentation logic (including for user interface visualization), business logic (working or processing logic) and remote services. If necessary the layers can be distributed in a flexible manner across machine or computer boundaries. In the case of tasks that are designed to be used by a plurality of workplaces the presentation logic is separated from the business logic such that only the presentation logic is installed on the clients (workplace computers) and the business logic is held and maintained centrally e.g. on a server. In the case of tasks that are used at image acquisition machines all the layers are used on the acquisition machine in order to maintain full functional capability in the event of a network failure and in non-networked environments such as e.g. small medical practices.

Individual tasks are interconnected to form taskflows. At the present time, however, the taskflow engines are not able or possibly able only with difficulty to work with tasks whose layers are distributed in different ways.

SUMMARY

In at least one embodiment of the present invention, a method or a device are disclosed which overcomes the above-cited problem.

A method and a device are disclosed. Advantageous embodiments of the method and of the device are the subject matter of the dependent claims or can be derived from the following description and the example embodiments.

At least one embodiment of the invention provides that the tasks can be interconnected to form a taskflow even if their software layers or units are distributed in different ways.

One aspect of at least one embodiment of the invention is a taskflow unit including at least one device and/or module for controlling computer-aided medical tasks within a medical computer network which are assigned to different software units, wherein the tasks are merged or have been merged into at least one taskflow within the medical computer network.

In at least one embodiment, the different software units can be installed on one computer and/or on different computers within the computer network.

In at least one embodiment, the taskflow unit is installed on an application server within the computer network.

According to at least one embodiment of the application, the software units can in each case comprise presentation logic preferably for user interface visualization and/or business logic and/or a remote service.

The unit can also have at least one device and/or module for sending messages for control purposes between the task unit and a software unit. In this case the messages are provided with a modifiable XML description.

A further aspect of at least one embodiment of the invention is directed to a method for controlling computer-aided medical tasks within a medical computer network, which tasks are assigned to different software units, wherein the tasks are merged to form at least one taskflow within the medical computer network, the control function preferably being performed by a taskflow unit (1) which is installed in particular on an application server (2) within the computer network.

The tasks can be controlled by way of the aforementioned messages being sent between the taskflow unit (1) and a software unit.

BRIEF DESCRIPTION OF THE DRAWINGS

Further advantages, details and developments of the invention will emerge from the following description of example embodiments in conjunction with the drawings, in which:

The FIGURE shows by way of example in a schematic representation a taskflow including tasks having different layer distribution architectures.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The FIGURE shows by way of example in a schematic representation a taskflow including tasks having different layer distribution architectures.

The following tasks are shown in the FIGURE:

A taskflow engine (Taskflow Engine) 1 is preferably installed on an application server 2. An application client 3 (identified as "AppClient1" in the example embodiment of FIG. 1) at an imaging system or modality receives at least one task, identified by T2 "Send Acquisition Frontend Configuration File" or T1 "Send Acquisition Backend Configuration File", from the taskflow engine for the presentation logic UI for use of a user presentation and for the business logic BizLogic for processing workflows. In the case of the application client 3, the presentation logic and the business logic are installed on one machine. In the case of the application client 4, called AppClient2, for preprocessing (Preprocessing) and AppClient3 for reading (Reading), the presentation logic and the business logic are installed on different machines 4 and 2. For that purpose the taskflow engine 1 sends the tasks T3 "Send Preprocessing Backend Config File" to the server 2 and T4 "Send Preprocessing Frontend Config File" to the application client ApplClient2. In addition the taskflow engine 1 sends the tasks T5. "Send Reading Backend Config File" to the server 2 and T6 "Send Reading Frontend Config File" to the application client ApplClient 3.

An embodiment of the invention includes at least one of the following advantageous properties and effects:

Individual taskflow steps can be performed in a coordinated manner by individual tasks on different machines.

Seamless transitions between the tasks in the taskflow are ensured:

In the case of transitions, in contrast to currently possible approaches, no taskflow status and no DICOM objects (DICOM=Digital Imaging and Communications in Medicine) are transmitted between machines.

Erroneous multiple performance of the taskflow steps on different machines is ruled out during transitions by way of the taskflow engine according to an embodiment of the invention.

Tasks which are configured for fault tolerance (presentation logic and business logic on one machine) and tasks which are configured for user friendliness (presentation logic on client machines and business logic on the server machine) can be interconnected to form one taskflow.

Each task that is specified by way of an XML description (XML=Extensible Markup Language) includes the details relating to presentation logic, business logic and remote services.

Each taskflow that is specified by way of an XML description includes the details relating to the interconnection of the tasks via their ports, to the activation strategies of the tasks (e.g. activation after startup, activation after arrival of the data at a specific port etc.) and to the data flow within the taskflow.

The taskflow engine according to an embodiment of the invention is used on the application server.

The business logic and presentation logic (=User Interface=UI in the FIGURE) of a task can be distributed arbitrarily between application server AppServer and application client AppClient 1, 2 or 3.

The business logic and presentation logic of a task register with the taskflow engine via a communication system.

The taskflow engine causes the business logic and presentation logic to execute by transmitting corresponding XML descriptions via the communication system to machines on which corresponding task layers are installed. No assumptions concerning on which machine the layers are installed are made in the taskflow engine.

The business logic and presentation logic are able to process the XML descriptions, load the components specified therein and synchronize themselves with the opposite party.

The taskflow engine is able to handle the data exchange between the tasks via their ports.

In this case an input port of a task can be fed by a plurality of output ports.

It is possible to activate tasks on the basis of a data flow. When the data arrives at specific ports the taskflow engine can place a task into an active state.

If an input port of a task is fed by a plurality of output ports of other tasks, the taskflow engine can also perform the activation when the data of some of the connected output ports has arrived (partial data availability). Partial data availability/full data availability is a configurable setting in the XML taskflow description.

In at least one embodiment, the invention is directed to a taskflow unit, comprising: at least one of a device and module for controlling computer-aided medical tasks within a medical computer network which are assigned to different software units, wherein the tasks are merged to form at least one taskflow within the medical computer network. In at least one embodiment, the different software units are installed on one computer within the computer network. In at least one other embodiment, the different software units are installed on different computers within the computer network. Further, in at least one embodiment, the taskflow unit is installed on an application server within the computer network.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

1 Taskflow engine (Taskflow Engine)
2 Application server (AppServer)
3 Application client (AppClient1)
4 Application client (AppClient2, AppClient3)
UI Presentation logic
BizLogic Business logic

What is claimed is:
1. A server, comprising:
a processor to implement:
an activation strategy of at least one taskflow;
a taskflow engine for controlling computer-aided medical tasks within a medical computer network, the medical tasks being performed by different software units, wherein the medical tasks are merged to form the at least one taskflow based on an interconnection of the software units via respective ports within the medical computer network; wherein if an input port of a software unit performing a task is fed by a plurality of output ports of a software unit performing other tasks, the taskflow engine performs activation when data of at least one of the output ports is received at the input port;
and
data flow within the taskflow, wherein the software units each include presentation logic for at least one of user interface visualization, business logic and a remote service, and the at least one of the presentation logic, business logic and remote service are distributed on a plurality of computers within the medical computer network, wherein the server is an application server and the processor controls sending at least one configuration file to a client device within the medical computer network for use by the client device for processing workflows.

2. The server as claimed in claim 1, wherein no taskflow status and no DICOM object is transmitted by the taskflow engine.

3. The server as claimed in claim 1, wherein the medical tasks comprise different layer distribution architectures.

4. The server as claimed in claim 1, wherein the taskflow engine is installed on an application server within the computer network.

5. The server as claimed in claim 1, wherein the taskflow is a processing sequence of at least one medical task.

6. The server as claimed in claim 1, wherein the taskflow engine includes at least one of a device and module for sending messages for control purposes between the taskflow engine and at least one of the different software units.

7. The server as claimed in claim 6, wherein the messages are provided with a modifiable XML description.

8. The server as claimed in claim 1, wherein the computer-aided medical tasks are separable such that at least one computer-aided medical tasks is shared among a plurality of client devices.

9. The server as claimed in claim 1, wherein the computer-aided medical tasks are installed on different computers within the computer network and the processor is configured to interconnect the computer-aided medical tasks to form a taskflow.

10. A method of controlling computer-aided medical tasks within a medical computer network, comprising:
    assigning computer-aided medical tasks to different software units that perform the medical tasks via a processor; and
    an activation strategy of at least one computer-aided medical task;
    merging the computer-aided medical tasks to form at least one taskflow based on an interconnection of the software units via respective ports within the medical computer network via the processor, wherein if an input port of a software unit performing a task is fed by a plurality of output ports of a software unit performing other tasks, the taskflow engine performs activation when data of at least one of the output ports is received at the input port, and data flow within the taskflow, wherein the software units each include presentation logic for at least one of user interface visualization, business logic and a remote service, and the at least one of the presentation logic, business logic and remote service are distributed on a plurality of computers within the medical computer network, wherein the processor controls sending at least one configuration file to a client device within the medical computer network for use by the client device for processing workflows.

11. The method as claimed in claim 10, wherein the controlling is performed by a taskflow engine which is installed on an application server within the computer network.

12. The method as claimed in claim 10, further comprising:
    forming a taskflow from computer-aided medical tasks installed on different computers within the computer network.

13. The method as claimed in claim 10, wherein the merging of the computer-aided medical tasks includes merging medical tasks having different layer distribution architectures.

14. The method as claimed in claim 11, further comprising:
    sending messages between the taskflow engine and at least one of the different software unit to control the computer-aided medical tasks.

15. The method as claimed in claim 14, further comprising:
    providing the messages with a modifiable XML description.

16. The method as claimed in claim 1, wherein no taskflow status and no DICOM object is transmitted by the taskflow engine.

17. A non-transitory computer readable medium including program segments for, when executed on a computer device, causing the computer device to implement the method of claim 10.

* * * * *